United States Patent [19]

Min et al.

[11] Patent Number: 4,718,903
[45] Date of Patent: Jan. 12, 1988

[54] ARTIFICIAL HEART

[75] Inventors: Byoung G. Min; Chang-Soon Koh; Jun-Lyang No; Gil-Jung Chun; Hi-Chan Kim; Dong-Chul Han; Sung-Wan Kim, all of Seoul, Rep. of Korea

[73] Assignee: Seoul National University Hospital, Seoul, Rep. of Korea

[21] Appl. No.: 906,849

[22] Filed: Sep. 15, 1986

[30] Foreign Application Priority Data

Sep. 18, 1985 [KR] Rep. of Korea .................. 6828

[51] Int. Cl.[4] ............................................. A61F 2/22
[52] U.S. Cl. ........................................ 623/3; 417/413
[58] Field of Search ................ 623/3; 417/412, 413, 417/410, 475

[56] References Cited

U.S. PATENT DOCUMENTS

| 3,520,641 | 11/1968 | Casey | 417/412 |
| 3,842,440 | 10/1974 | Karlson | 417/412 |
| 4,058,857 | 11/1977 | Runge et al. | 623/3 |
| 4,468,177 | 8/1984 | Strimling | 623/3 |
| 4,545,744 | 10/1985 | Weber | 417/475 |

Primary Examiner—Richard J. Apley
Assistant Examiner—James Prizant
Attorney, Agent, or Firm—Kerkam, Stowell, Kondracki & Clarke

[57] ABSTRACT

An artificial heart blood pump including a driving motor which can be contained within the human body and which performs pumping action when supplied from an electric power source from outside of the human body. The pump includes left and right ventricles defined by elastomeric films fixed inside a pump body near each side. Each ventricle has an inlet and an outlet provided with respective check valves. Within the pump body generally between the elastomeric films is a movable body having a cylindrical case with a bidirectional driving motor built in. The movable body rolls from side to side during operation to alternately press against the elastomeric films and discharge blood alternately from the ventricles. To cause the movable body to roll from side to side, the movable body has an end portion rotatably connected to each end of the cylindrical case, and the end portions each have a groove slidably engaging a side guide rail on inner surfaces of the pump body so as to prevent rotation of the end portions within and relative to the pump body. Power transmitting means, preferably in the form of a pair of planetary gear trains, connects a motor shaft to one of the end portions so as to provide bidirectional relative rotation between the cylindrical case and the one end portion such that the cylindrical case rotates within the pump body. To convert this rotation to side-to-side rolling, a semi-circumferential row of gear teeth on said cylindrical case engages a toothed rack on an inner surface of the pump body.

4 Claims, 9 Drawing Figures

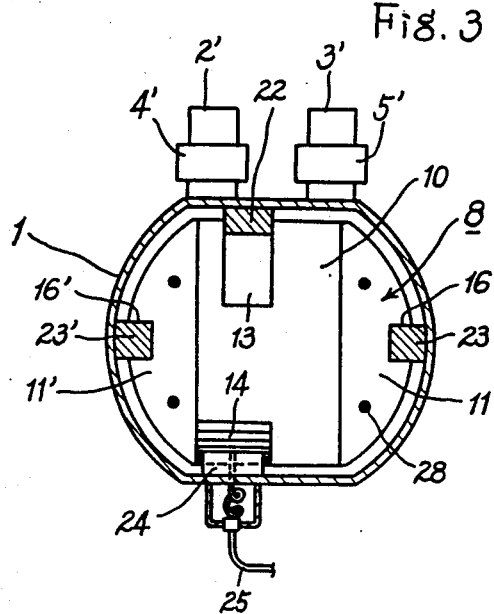
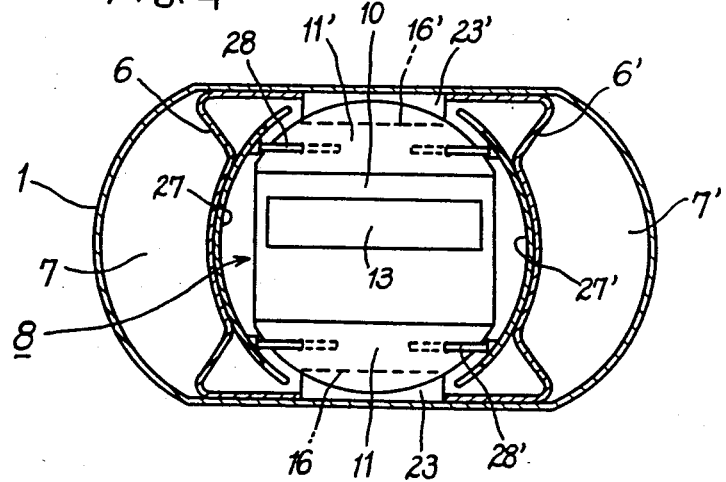

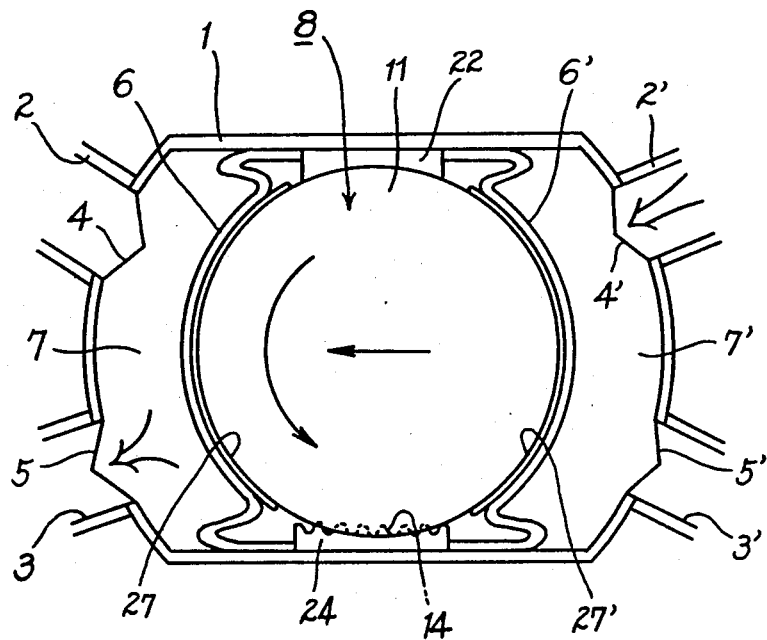

ARTIFICIAL HEART

BACKGROUND OF THE INVENTION

The present invention relates to a blood pump in an artificial heart designed to replace a natural heart. An LVAD (left ventricle assist device) is used to support the function of the natural heart when it is found difficult to maintain a person's life only by the natural heart due to a worsened heart disease. A TAH (total artificial heart) is used to completely replace the function of the natural heart.

An ultimate goal in artificial heart development is to have an energy conversion device, a controller and an energy source all within the human body. A known TAH is equipped with a large-sized pneumatic-type blood pumping device outside of the body, and this makes it inconvenient to walk or to carry.

SUMMARY OF THE INVENTION

To overcome this disadvantage, by the present invention there is provided an artificial heart with a built-in blood pump which is able to perform the function of energy conversion in the human body when powered by an electric source from outside of the human body.

Accordingly, it is an object of the invention to provide an artificial heart blood pump including a driving motor which can be contained within the human body and which performs pumping action when supplied from an electric power source from outside of the human body.

Briefly stated and in accordance with the invention, the foregoing and other objects are attained by an artificial heart pump structure in which left and right ventricles are defined by elastomeric films fixed inside a pump body near each side. Each ventricle has an inlet and an outlet provided with respective check valves. Within the pump body generally between the elastomeric films is a movable body having a cylindrical case with a bidirectional driving motor built in. The movable body rolls from side to side during operation to alternately press against the elastomeric films and discharge blood alternately from the ventricles.

To cause the movable body to roll from side to side, the movable body has an end portion rotatably connected to each end of the cylindrical case, and the end portions each have a groove slidably engaging a side guide rail on inner surfaces of the pump body so as to prevent rotation of the end portions within and relative to the pump body. Power transmitting means, preferably in the form of a pair of planetary gear trains, connects a motor shaft to one of the end portions so as to provide bidirectional relative rotation between the cylindrical case and the one end portion such that the cylindrical case rotates within the pump body. To convert this rotation to side-to-side rolling, a semi-circumferential row of gear teeth on said cylindrical case engages a toothed rack on an inner surface of the pump body.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

FIG. 3 is a sectional view taken along line B—B of FIG. 2;

FIG. 4 is a sectional view taken along line C—C of FIG. 2;

FIG. 9 is a schematic view depicting the operation of the blood pump of the invention.

DETAILED DESCRIPTION

Figure 1:
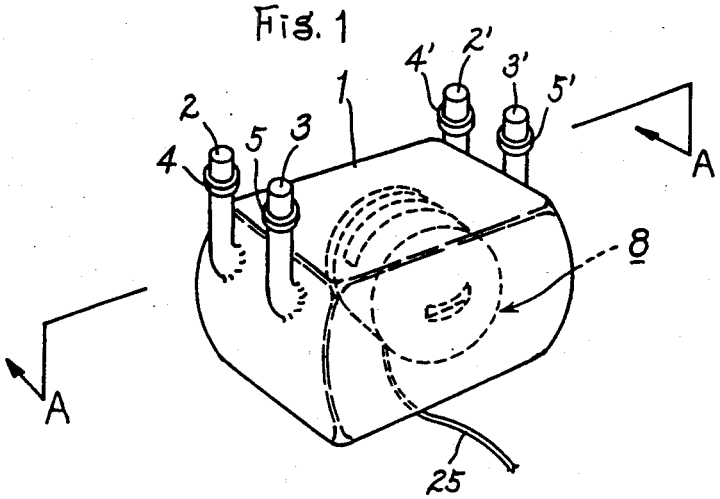
FIG. 1 is a perspective view of a pump in accordance with the present invention.

Referring now to the drawings, a hollow pump body 1 is formed of stainless steel and is provided with a pair of inlets 2 and 2' and a pair of outlets 3 and 3' for connection to blood vessels, there being an inlet and an outlet on each side. The inlets 2 and 2' and outlets 3 and 3' are respectively equipped with inlet check valves 4 and 4' and outlet check valves 5 and 5' which open only in the desired direction of blood movement.

Figure 2:
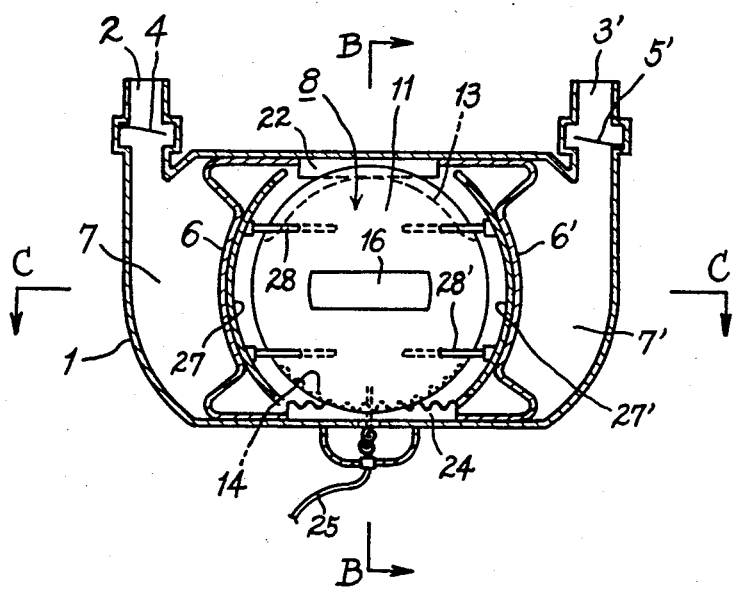
FIG. 2 is a cross sectional view taken along line A—A of FIG. 1.

As best seen in FIGS. 2 and 4, within the pump body 1, elastomeric films 6 and 6', preferably formed of silicon rubber, are fixed on both sides to define, together with inner side walls of the body 1, left and right ventricles 7 and 7'. Within and in the center of the pump body 1, between the elastomeric films 6 and 6', a movable body 8 is positioned and causes pumping action by rolling from side to side and alternately pressing the elastomeric films 6 and 6' towards the sides of the left and right ventricles 7 and 7'.

The movable body 8 comprises a bidirectional drive motor 9, a cylindrical case 10 surrounding the motor 9, and two semispherical end portions 11 and 11'.

The cylindrical case 10 is fixed onto the body of the motor 9 by means of a key 12, so the motor 9 and the cylindrical case 10 comprise one united body. A semi-circumferential guide groove 13 is provided on the upper circumference of the cylindrical case, in which a body guide rail 22 (explained hereinbelow with reference to FIG. 3) is inserted. A semi-circumferential body gear 14 on the cylindrical case 10 diametrically opposite the guide groove 13 engages a rack 24 (also explained hereinbelow with reference to FIG. 3). An annular ring gear 15 having internal teeth is formed on the inner curcumference at one end of the cylindrical case 10, the end towards the right side portion 11.

The two end portions 11 and 11' are rotatably assembled with the cylindrical case 10 so as to rotate independently with respect to the cylindrical case 10. These end portions 11 and 11' are provided with grooves 16 and 16' which slidably engage side guide rails 23 (described hereinbelow with reference to FIG. 3).

A power transmitting means is provided in the body case 10. This power transmitting means generally serves to connect a shaft of the motor 9 to the end portion 11 so as to provide bidirectional relative rotation between said cylindrical case 10 and the end portion 11. The power transmitting means more particularly comprises first and second planetary gear trains arranged generally in tandem, with the annular ring gear 15 serving both of the planetary gear trains.

The first planetary gear train includes a first driving gear 17 fixed to the motor shaft and serving as a first sun gear, and a first set of three planet gears 18, 18' and 18" rotatably and drivingly connected to and carried by a base plate 19 so that the gears 18, 18' and 18" engage the first driving gear 17 and the annular ring gear 15. The second planetary gear train includes a second driving gear 20 connected to the base plate 19 and serving as a second sun gear, and second set of three planet gears 21, 21' and 21" drivingly connected to and carried by the side portion so that the gears 21, 21' and 21" engage the second driving gear 20 and the annular ring gear 15.

As best seen in FIG. 3, the movable body 8 is installed in the hollow pump body 1 with the guide groove 13 on its upper side slidably engaged with the body guide rail 22 extending along an inner wall of the pump body 1, and the grooves 16 and 16' on its end portions slidably engaged with the side guide rails 23 and 23' also extending along an inner wall of the pump body 1.

Figure 5:
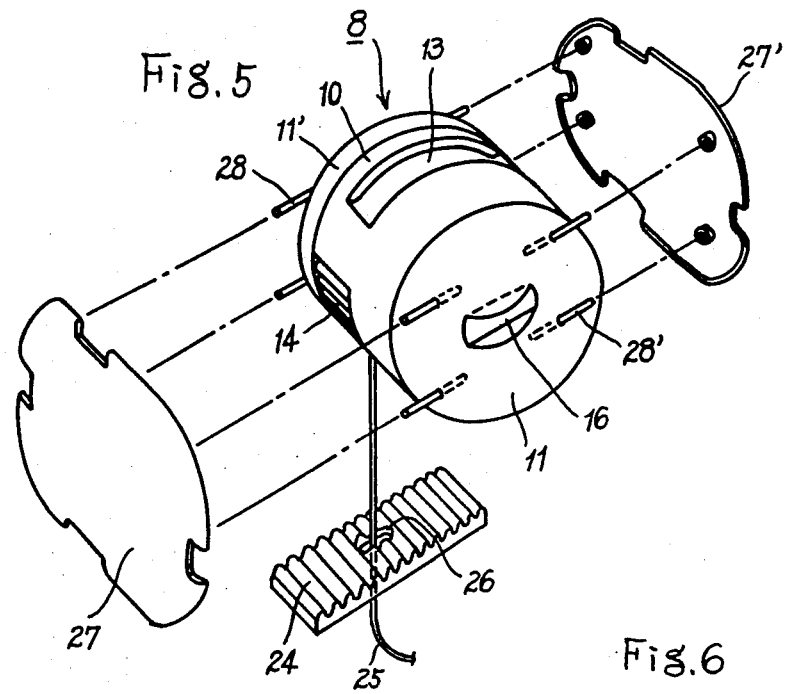
FIG. 5 is a perspective view showing an important part of the present invention partly disassembled.
Figure 6:
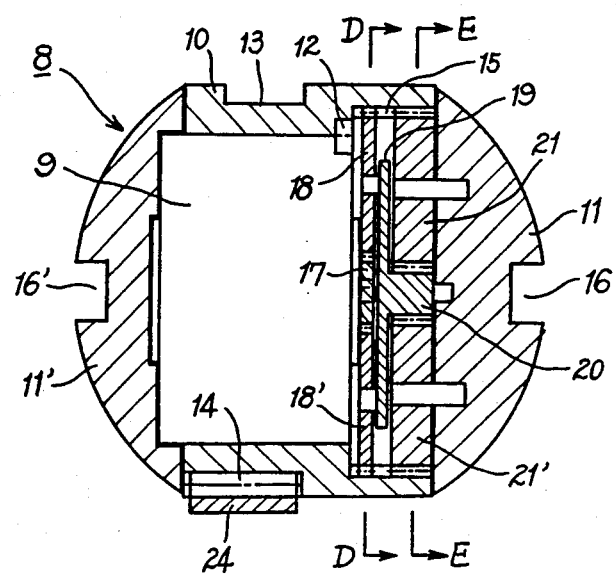
FIG. 6 is a sectional view of the globular movable body of the present invention.
Figure 7:
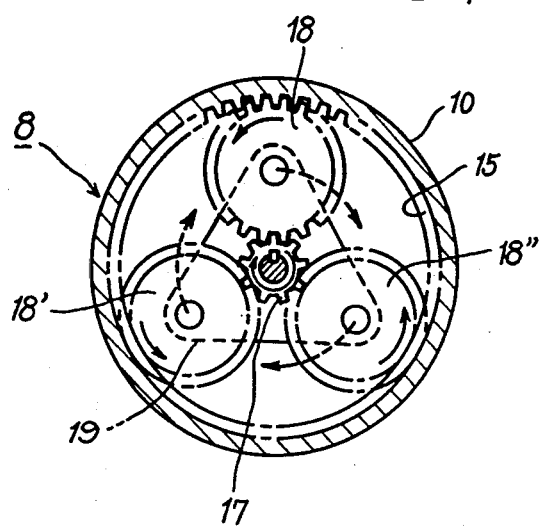
FIG. 7 is a sectional view taken along line D—D of FIG. 6.
Figure 8:
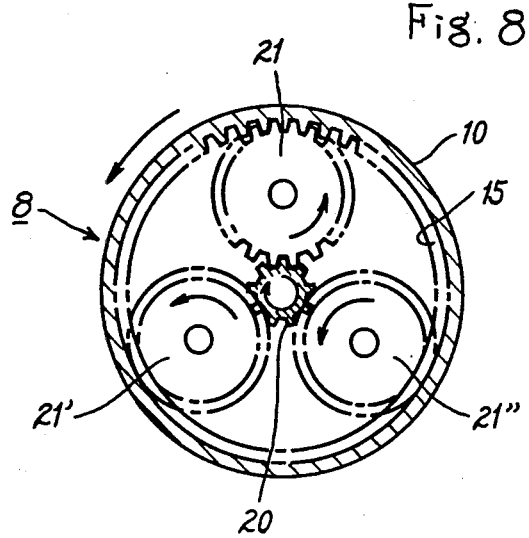
FIG. 8 is a sectional view taken along line E—E of FIG. 6.

The body gear 14 formed on the lower circumferential wall of the cylindrical case 10 of the movable body 8 is installed so as to engage the rack 24, extending along the inner bottom within the pump body 1. A wire 25 extends from the driving motor 9 through the cylindrical case 10 and passes to the outside through an aperture 26 (FIG. 5) in the rack 24, for connection to an electric power source outside of the human body, such as a battery.

The movable body 8 is installed between the elastomeric films 6 and 6' on both sides of the interior of the pump body 1 with semi-spherical buffer plates 27 and 27' interposed therebetween. The buffer plates 27 and 27' serve to keep the elastomeric films 6 and 6' from being damaged by coming into direct contact with the movable body 8. The buffer plates 27 and 27' are respectively connected to the side portions 11 and 11' of the movable body 8 by four connecting pins 28 and four connecting pins 28'. As may be seen in FIG. 5, so the buffer plates 27 and 27' are not caught by the body guide rail 22, the side guide rails 23 and 23', or the rack 24 as the buffer plates 27 and 27' move with the movable body 8 as the movable body rolls from side to side, suitable clearance notches are provided on the upper and lower sides and on the left and right sides of the buffer plates 27 and 27'.

The operation of the present invention will now be described.

When the driving motor 9 in the movable body 8 is supplied with electric current through the wire 25 from a source outside the body, the shaft of the motor 9 rotates in a fixed cycle repeatedly in one and then the opposite direction by means of a conventional motor control circuit (not shown).

As shown in FIGS. 6–9, when the shaft of driving motor 9 rotates in a clockwise direction, the first driving gear 17 fixed thereon also rotates in a clockwise direction. The first set of three planet gears 18, 18' and 18" engaged therewith rotate about their individual axes in a counterclockwise direction and, at the same time, jointly rotate in a clockwise direction while engaging the annular ring gear 15 of the cylindrical case 10. The base plate 19 is driven by the gears 18, 18' and 18" and thus also rotates in a clockwise direction, and the second driving gear 20 accordingly rotates clockwise. As the second driving gear 20 rotates in a clockwise direction, the second set of three planet gears 21, 21' and 21" engaged therewith rotate about their individual axes in a counterclockwise direction and, at the same time, jointly rotate in a clockwise direction while engaging the annular ring gear 15 of the cylindrical case 10. The side portion 11 is thus driven in a clockwise direction.

The rotary motion thus produced is converted to a driving force which turns annular ring gear 15 of the cylindrical case 10 because the three planet gears 21, 21' and 21" of the second set are axially fixed onto the right side portion 11 of the movable body 8 and the right side portion 11 is unable to rotate because the side guide rail 23 is slidably engaged with the guide groove 16. As a result, the gears 21, 21' and 21" only rotate on their axes and rotate the cylindrical case 10 in a counterclockwise direction. When the cylindrical case 10 rotates in a counterclockwise direction, the body of the driving motor 9 fixed with the key 12 onto the cylindrical case 10 also rotates in the same direction.

The driving power generated by the motor 9 is transferred to the three gears 21, 21' and 21" of the second set engaged with the annular ring gear 15 of the cylindrical case 10 and induces the rotation of the gears 21, 21' and 21". Since these second gears 21, 21' and 21" are connected to the side portion 11, the cylindrical case 10 is rotated by the rotation of the second gears. At this time, as the left side plate 11' of driving motor 9 is also kept from turning because the left side guide rail 23' is inserted into guide groove 16', the cylindrical case 10 turns together with the body of driving motor 9.

As stated hereinabove, the body gear 14 formed in the lower side thereof engages the rack 24 of pump body 1. When the cylindrical case 10 turns, the whole of the movable body 8 rolls to either ventricle 7 or 7' of the pump body 1. A part of the cylindrical case 10 of the movable body, 8 is guided by the body guide rail 22 inserted into the upper groove 13 and continues to rotate, and both side portions 11 and 11' are kept from turning by the side guide rails 23 and 23' slidably engaging the grooves on both sides 16 and 16'.

When the movable body 8 moves towards one of the heart ventricles 7 or 7', the buffer plates 27 and 27' connected to the cases on both portions 11 and 11' by connecting pins 28 and 28' also move and press one of the elastomeric films 6 or 6' which forms the ventricle 7 or 7' For example, when the movable body 8 rolls to the left ventricle 7, the elastomeric film pressed by buffer plate 27 discharges the blood from the left ventricle through the outlet 3 and outlet valve 5. At the same time, blood is drawn into the right ventricle 7' through inlet valve 4' and inlet 2' because suction is produced by the withdrawal of movable body 8. Thus, a single operation cycle is completed.

When an operation cycle is completed, the driving motor 9 is switched to the opposite direction of rotation. Then, the movable body 8 rolls in an opposite direction. As rubber film 6' on the side of the right ventricle 7' is put under pressure this time, the movable body 8 discharges the blood in the right ventricle 7' through outlet valve 5' and outlet 3' and draws the blood into the left ventricle 7 through inlet 2 and inlet valve 4.

Thus, continuous blood pumping operation is performed by an alternating motion of the movable body 8 at a continued pace. When the blood pump for use in an artificial heart is made to operate according to the present invention, it is operable when pump body and pumping driver with a small motor is built in the body and electric power is supplied to the motor from the outside of the body through a wire. Thus, the pumping device can be made so small as to be contained within a human body, and a battery can easily be carried as an electric source so that the present invention produces an improved effect by making the activity of the affected human body almost as free as that of a normal person.

What is claimed is:

1. An artificial heart comprising:

a hollow pump body having two sides, at each side there being an inlet provided with an inlet valve and an outlet provided with an outlet valve, said pump body having a body guide rail, a pair of opposed side guide rails, and a toothed rack opposite said body guide rail, all extending along inner surfaces of said pump body in a side-to-side direction;

elastomeric films attached to the inner surface of said pump body near the sides so as to define, together with the side walls of said pump body, left and right ventricles;

a movable body within said pump body generally between said elastomeric films, said movable body including a cylindrical case, an end portion rotatably connected to each end of said cylindrical case, said cylindrical case having a semi-circumferential guide groove slidably engaging said body guide rail, said cylindrical case having a semi-circumferential row of body gear teeth diametrically opposite said guide groove engaging said toothed rack, and said end portions each having a groove slidably engaging a respective one of said side guide rails so as to prevent rotation of said end portions within and relative to said pump body;

buffer plates generally interposed between said movable body and said elastomeric films, said buffer plates being connected to said end portions;

a bidirectional drive motor located within said cylindrical case and having a shaft, said drive motor fixed to said cylindrical case such that relative rotation therebetween is prevented; and power transmitting means connecting said motor shaft and one of said end portions so as to provide bidirectional relative rotation between said cylindrical case and said one of said end portions;

whereby as said drive motor rotates in one direction causing relative rotation between said cylindrical case and said one of said end portions, said cylindrical case rotates within said pump body and said body gear teeth engaging said toothed rack cause said movable body to roll towards one side such that one of said buffer plates presses against one of said elastomeric films to discharge blood from one of said ventricles, and as said drive motor rotates in the opposite direction said movable body rolls towards the other side such that the other of said buffer plates presses against the other of said elastomeric films to discharge blood from the other of said ventricles.

2. An artificial heart in accordance with claim 1, wherein said power transmitting means comprises:

an annular ring gear with internal teeth formed at one end of said cylindrical case;

first and second planetary gear trains, said annular ring gear serving both of said planetary gear trains;

said first planetary gear train including:
a first driving gear connected to said drive motor shaft and serving as a first sun gear, and
a first set of three planet gears rotatably and drivingly connected to and carried by a base plate, the planet gears of said first set engaging said first driving gear and said annular ring gear; and said second planetary gear train including:
a second driving gear connected to said base plate and serving as a second sun gear, and
a second set of three planet gears rotatably and drivingly connected to and carried by said one of said end portions, the planet gears of said second set engaging said second driving gear and said annular ring gear.

3. An artificial heart in accordance with claim 1 wherein said elastomeric films comprise silicon rubber.

4. An artificial heart in accordance with claim 2 wherein said elastomeric films comprise silicon rubber.

* * * * *